(12) United States Patent
Ancira et al.

(10) Patent No.: US 7,381,427 B2
(45) Date of Patent: Jun. 3, 2008

(54) SEBORRHEIC KERATOSIS TREATMENT

(75) Inventors: Margaret Ancira, Phoenix, AZ (US); Mickey Miller, 5855 E. Mockingbird La., Paradise Valley, AZ (US) 85253

(73) Assignee: Mickey Miller, Paradise Valley, AZ (US)

( * ) Notice: Subject to any disclaimer, the term of this patent is extended or adjusted under 35 U.S.C. 154(b) by 120 days.

(21) Appl. No.: 10/684,136

(22) Filed: Oct. 9, 2003

(65) Prior Publication Data

US 2004/0137077 A1  Jul. 15, 2004

Related U.S. Application Data

(63) Continuation-in-part of application No. 10/072,829, filed on Feb. 8, 2002, now Pat. No. 7,138,146.

(60) Provisional application No. 60/267,978, filed on Feb. 9, 2001.

(51) Int. Cl.
*A61K 33/40* (2006.01)
(52) U.S. Cl. .................. 424/616; 514/251; 514/276; 514/356; 514/474
(58) Field of Classification Search ................ 424/616; 514/251, 276, 356, 474
See application file for complete search history.

(56) References Cited

U.S. PATENT DOCUMENTS

| | | | |
|---|---|---|---|
| 3,949,072 A * | 4/1976 | Tenta | 424/642 |
| 3,954,974 A | 5/1976 | Herzog et al. | |
| 4,018,802 A | 4/1977 | Cragoe, Jr. et al. | |
| 4,112,121 A * | 9/1978 | Tenta | 514/731 |
| 4,128,564 A | 12/1978 | Cragoe, Jr. et al. | |
| 4,438,102 A | 3/1984 | Ganci | |
| 4,485,091 A | 11/1984 | Fitton | |
| 4,826,681 A | 5/1989 | Jacquet et al. | |
| 5,362,915 A | 11/1994 | Maschler et al. | |
| 5,380,764 A | 1/1995 | Herzog | |
| 5,472,715 A | 12/1995 | Uehara | |
| 5,594,015 A | 1/1997 | Kurtz et al. | |
| 5,736,582 A | 4/1998 | Devillez | |
| 5,824,694 A | 10/1998 | Kurtz et al. | |
| 5,958,984 A | 9/1999 | Devillez | |
| 6,028,104 A | 2/2000 | Schmidt et al. | |
| 6,146,640 A | 11/2000 | Kyke | |

FOREIGN PATENT DOCUMENTS

GB  2285218  7/1995

OTHER PUBLICATIONS

Lee and Choi, "TCA chemical peeling. Procedures, complication and self-evaluation of therapeutic effect in 242 patients," Korean Journal of Dermatology, 31:1-8, 1993 (abstract only).
Beitler et al., "Association between acrochordons and colonic polyps," *J. Am. Acad. Dermatol.*, 14: 1042-1044, 1986.
Bilottia and Waye, "Hydrogen Peroxide Enteritis: the Snow White Sign," *Gastrointestinal Endoscopy*, 35: 428-430, 1989.
Caro, Marcus Rayner; and Szymanski, Frederick J.: Seborrheic and Senile Keratoses. *Medical Clinics of North America* 35: 419-431; 1951.
Cashmore, Robert W.; and Perry, Harold O.: Differentiating Seborrheic Keratosis from Skin Neoplasm. *Geriatrics* 40: 69-75; 1985.
Christensen et al., "Fatal Oxygen Embolization after Hydrogen Peroxide Ingestion," *Critical Care Medicine*, 20(4): 543-544, 1992.
Cornell and Stoughton, "Correlation of the vasoconstriction assay and clinical activity in Psoriasis," *Arch Dermatol.*, 121: 63-67, 1985.
Danis Bodeur, "The Danger of Hydrogen Peroxide as a Colonic Irrigating Solution," *Journal of Pediatric Surgery*, 2(2): 131-133; 1967.
Dickson et al., "Hydrogen peroxide exposure—325 exposures reported to a regional poison control center," *Clinical Toxicology*, 32(6): 705-714, 1994.
Eberlin, J.L.: Curetting for Seborrheic Keratoses. *Plastic and Reconstructive Surgery* 101(2): 546-547; 1998.
Ellis et al., "Increased epidermal growth factor receptors in seborrheic keratoses annd acrochordons of patients with the dysplastic nevus syndrome," *J. Am. Acad. Dermatol*, 23: 1070-1077, 1990.
Giberson et al., "Near-fatal hydrogen peroxide ingestion," *Annals of Emergency Medicine*, 18: 119-120/778-779, 1989.
Goette et al., "Skin Blanching Induced by Hydrogen Peroxide," *Southern Medical Journal*, 70(5): 620-622, 1977.
Goette, "Hydrogen peroxide-induced skin blanching," *Arch Dermatol.*, 112: 1788-1789, 1976.
Gruber et al., "The effect of commonly used antiseptics on wound healing," *Antiseptics ad Wound Healing*, 55(4): 472-476, 1975.
Henry et al., "Hydrogen Peroxide 3% Exposures," *Clinical Toxicology*, 34(3): 323-327, 1996.
Hocutt, "Skin cryosurgery for the family physician," *American Family Physicians*, 48: 445-452, 1993.
Humberston et al., "Ingestion of 35% Hydrogen Peroxide," *Clinical Toxicology*, 28(1): 95-100, 1990.
Jones-Caballero, M.; Peñas, P.F.; Buezo, G.F.; Fraga, J.; and Aragüés, M.: Malignant Melanoma Appearing in a Seborrhoeic Keratosis. *British Journal of Dermatology* 133: 1016-1018; 1995.
Klein-Szanto and Slaga,"Effects of Peroxides on Rodent Skin: Epidermal Hyperplasia and Tumor Promotion," *The Journal of Investigative Dermatology*, 79: 30-34, 1982.
Leavitt et al., "Skin tags: a cutaneous marker for colonic polyps," *Annals of Internal Med.*, 98: 928-930, 1983.
Mevorah, B.; and Mishima Y.: Cellular Response of Sseborrheic Keratosis Following Croton Oil Irritation and Surgical Trauma with Special Reference to Melanoacanthorma. *Dermatologica* 131: 452-464; 1965.
Mohs, Frederic E.: Seborrhoeic Keratoses: Scarless Removal by Curettage and Oxidized Cellulose. *Journal of the American Medical Association* 212(11): 1956-1958; 1970.

(Continued)

Primary Examiner—L Blaine Lankford
(74) Attorney, Agent, or Firm—Richard E. Oney; Lana M. Knedlik

(57) ABSTRACT

The subject of the present invention is seborrheic keratosis removal and prevention utilizing safe dependable effective biocompatible treatments with no scarring, bleeding, burning, freezing, shocking, and hypopigmentation or hyperpigmentation.

70 Claims, 1 Drawing Sheet

OTHER PUBLICATIONS

Nanney et al., "Altered distribution of phospholipase C-γ1 in Benign hyperproliferative epidermal diseases," *Cell Growth & Differentiation*, 3: 233-239, 1992.

Nanney et al., "Epidermal growth factor receptors in idiopathic and virally induced skin diseases," *Am. J. Pathology*, 140(4): 915-.

O'Toole et al., "Hydrogen Peroxide Inhibits Human Keratinocyte Migration," *Dermatology Surgery*, 22: 525-529, 1996.

Oliver and Murphy, "influenzal Pneumonia: the intravenous injection of hydrogen perioxide," *The Lancet*, 432-433, 1920.

Pumphrey, "Hydrogen peroxide procititis," *American J. of Surgery*, 81: 60-62, 1951.

Rathbun, "A Method for Removing the Acrochordon (Skin Tag)," *Kansas Medicine*, 91(1): 11-12, 1990.

Sebben, "The hazards of electrosurgery," *J. Am. Acad. Dermatol.*, 16(4): 869-872, 1987.

Segal, "Liquid nitrogen therapy," *Australian Family Physician*, 13: 356-357, 1984.

Sowden, J.M.; Lewis-Jones, M.S.; and Williams, R.B.: The Management of Seborrhoeic Keratoses by General Practicioners, Surgeons, and Dermatologists. *British Journal of Dermatology* 139:348-349; 1998.

Strohmer et al., "Use of hydrogen peroxide for vaginal contraception," *Human Reproduction*, 12: 1599, 1997.

Strother,"Acrochordonectomy Made Easy," *Cllinician Reviews*, 8(3): 154-155, 1998.

Tegner and Bjornberg, "Hydrogen Peroxide Cream for the Prevention of White Pressure Areas in UVA Sunbeds," *Acta Dermatologica Venereologica (Stockholm)*, 70: 75-76, 1990.

Tegner, "Induction of Skin Blanching by Hydrogen Peroxide," *Acta Dermatologica Venerologica (Stockholm)*, 74: 474-475, 1994.

Tur et al., "Topical hydrogen peroxide treatment of ischemic ulcers in the guinea pig: blood recruitment in multiple skin sites," *Journal of the American Academy of Dermatology*, 33: 217-221, 1995.

Wetmore, Stephen J.: Cryosurgery for Common Skin Lesions: Treatment in Family Physicians' Offices. *Canadian Family Physician* 45: 964-974; 1999.

Winklemann, R.K.: Superficial Spreading ( and Disappearing) Seborrhoeic Keratosis. *Cutis* 63: 235-237; 1999.

Yakar, Jona Ben; Sagi, Amiram; Mahler, Dan; and Zirkin, Howard: Malignant Melanoma Appearing in Seborrheic Keratosis. *Journal of Dermatologic Surgery and* Oncology 10: 382-383; 1984.

Answer and Counter Claim filed Dec. 2, 2003 in Physicians Choice of *Arizona, Inc. v. Mickey Miller*, CB-2003-020242 (Superior Court of Arizona, Maricopa County).

* cited by examiner

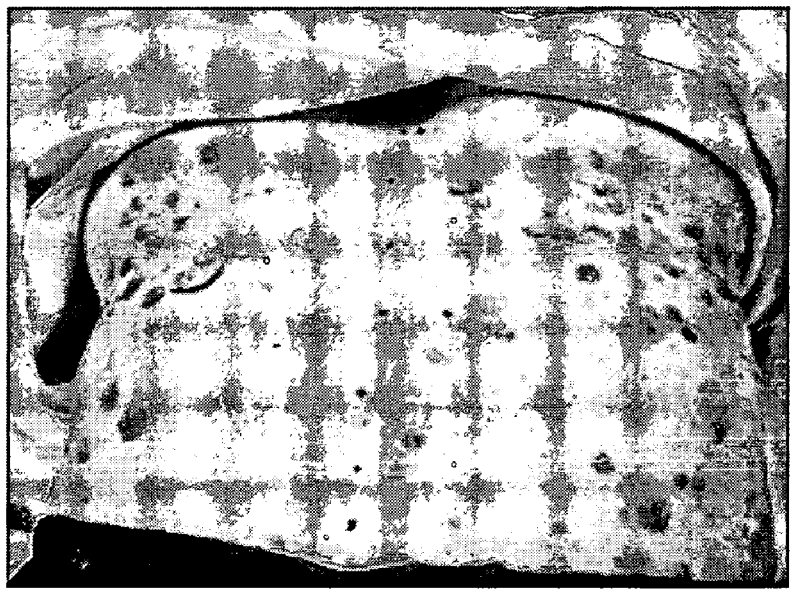
FIG. 1 Before Treatment
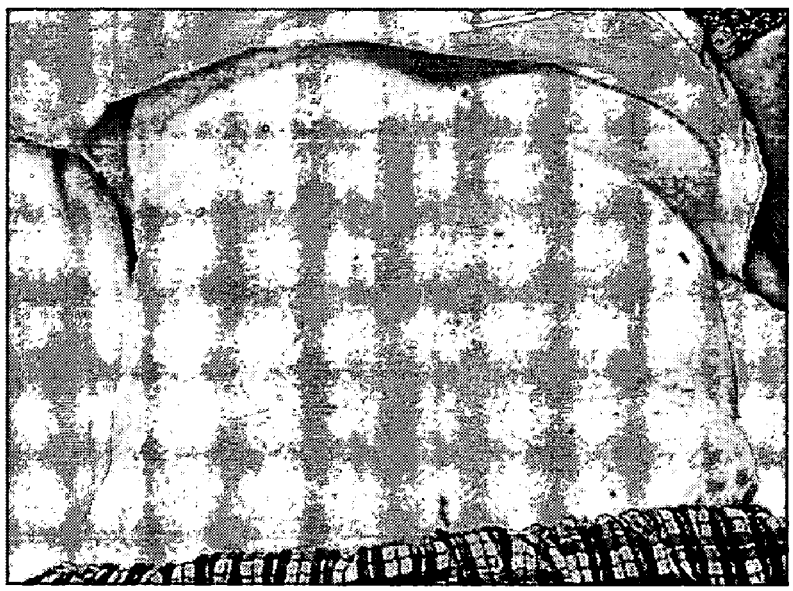
FIG. 2 After Treatment

SEBORRHEIC KERATOSIS TREATMENT

CROSS-REFERENCE TO RELATED APPLICATIONS

This application is a continuation-in-part application of U.S. patent application Ser. No. 10/072,829 filed on Feb. 8, 2002, now U.S. Pat. No. 7,138,146 which is a continuation-in-part application of U.S. Provisional Patent Application Ser. No. 60/267,978, filed Feb. 9, 2001.

BACKGROUND OF THE INVENTION

1. Field of the Invention

The present invention provides topical compositions and methods for the treatment, removal, elimination and prevention of seborrheic keratoses. More specifically, the present invention involves the use of high concentration hydrogen peroxide to treat the affliction.

2. Description of Related Art

Seborrheic keratoses are the most common benign lesions observed in humans. According to the U.S. National Health and Nutrition Examination Survey of 1995–1996, about 45 million persons in the United States have seborrheic keratoses with the distribution being about equal between the sexes. Seborrheic keratoses were described as early as 1864 by Virchow and in 1869 by Neumann, who called them senile warts. Seborrheic keratoses have also been described as senile verruca, pigmented verruca, keratosis pigmentosa, basal cell papilloma and a long list of other names in the medical literature.

Seborrheic keratoses may take a variety of forms, including but not limited to: dermatosis papulosa nigra, stucco, acanthotic, hyperkeratotic, dermatolipoma, verrucous, melanoacanthotic, reticular, adenoid, and clonal.

In general, seborrheic keratoses begin as small, round or oval, brownish macules. The sites of predilection are the face, scalp, trunk, particularly the interscapular and sternal regions and the backs of the hands. In rare cases, seborrheic keratoses have also been reported in the ear canal and the penis. Seborrheic keratoses do not occur on the palms of the hands or soles of the feet.

All lesions of seborrheic keratosis, whether small or large, show a sharp line of demarcation between the pathologic changes seen in the tumor and the normal adjacent skin.

In a small seborrheic keratosis, the epidermis at the border shows an abrupt elevation to produce many finger-like upward projections, each of which contains a central core of connective tissue. These digitations are covered by a loose non-nucleated scale which dips down to fill all of the intervening crevices and which forms a thick plug in each of the follicles.

As the keratosis grows larger the digitations elongate and they show an irregular cellular hyperplasia to produce anastomoses in many directions. This acanthosis results in the production of filiform branches and large epidermal masses and many intervening passages which are filled by extensions from the surface scale. In most cases, the granular layer is intact and there are no nuclei in the scale, but occasionally there are a few islands of parakeratosis. The basal layer is unbroken and the entire tumor lies superficial to a base that is level with that of the adjacent normal skin.

Seborrheic keratoses may grow to become quite large as illustrated by the report of the giant pedunculated seborrheic keratosis by Dr. Rudolf L. Baer. The patient was reported at the Department of Dermatology at the New York University School of Medicine, in the May 1979 issue of the Archives of Dermatology. The brown-ish lesion developed on the right inguinal region of a 75 year old woman and was allowed to grow for 40 years because of the lack of a convenient treatment such as the present invention for seborrheic keratosis elimination. The seborrheic keratosis, over a period of many years, gradually became larger, and eventually formed a pendulous mass measuring 5.5×3.5 centimeters. Due to the lack of an effective topical treatment such as the present invention, Dr. Baer had to remove the seborrheic keratosis with a scalpel while the patient was under local anesthesia with lidocaine and stop the bleeding by electrodesiccation. Microscopic examination of the gargantuan seborrheic keratosis revealed epidermal hyperplasia with horn pseudocysts, interweaving of the rete, and nuclei of uniform size and shape.

If left untreated, as the vast majority of seborrheic keratoses are, squamous cell carcinoma may arise as reported by Dr. Rudolf L. Baer in the November 1981 issue of the Journal of the American Academy of Dermatology. For some years, due to the lack of an effective self-applied treatment, a 73-year-old patient had allowed a seborrheic keratosis to grow on the left side of his trunk. Some months before consulting Dr. Baer, part of the growth fell off and then recurred with distinctly more elevation than the remainder of the seborrheic keratosis. The seborrheic keratosis was described as a verrucous, keratotic, gray-brown-black, sharply defined lesion with somewhat scalloped edges. The seborrheic keratosis measured 60×27 millimeters and was elevated about 3 mm above the surrounding normal skin. Two different components were within the seborrheic keratosis, one somewhat lighter and less elevated, slightly verrucous area and the second a lighter gray-brown 19×18 millimeter cauliflower-like area, elevated 9 millimeters above the surrounding normal skin. Treatment with the present invention would have prevented the emergence of the squamous cell carcinoma and eliminated the necessity of the lesion being excised with a surrounding margin of normal skin.

Multiple seborrheic keratosis treatment is not readily accomplished by techniques available in conventional practice; therefore, many people suffering with large numbers of seborrheic keratoses go many years with no treatment. Such is the case reported by Dr. Robert W. Cashmore and Dr. Harold O. Perry in the July, 1985 issue of *Geriatrics*. A 55-year-old Caucasian man had many, many darkly pigmented seborrheic keratoses on his trunk for twenty years. During the twenty years, he was seen for various medical problems, including and anxiety-tension state and preoccupation with bodily functions. During this period, he was seen eight times by a dermatologist for reassurance to alleviate his concern about the multiple seborrheic keratoses. At his last visit, a 1×2 centimeter erythematous lesion was noted among the numerous keratoses on his right shoulder, and this was thought clinically to be a superficial basal cell carcinoma. This impression was confirmed by biopsy. The fact that the man was untreated for twenty years after being examined eight times by a dermatologist and then allowed to develop cancer clearly points to the urgent need for an effective, practical treatment such as the present invention.

Early medical treatment modalities of seborrheic keratoses do not differ appreciably from the treatment choices offered by the majority of present day, medical practitioners with the exception of laser usage for seborrheic keratosis removal, which also results in adverse side effects such as scarring, hyperpigmentation and hypopigmentation.

The Jan. 30, 1915 issue of *The Journal of the American Medical Association* includes a report titled "The Symptomatology and Treatment of Seborrheic Keratoses" by the prominent Kansas City, Mo. physician Richard L. Sutton. A form of cryogenic therapy is described by Dr. Sutton using Pusey's carbon dioxide snow and a 5 percent ammoniated mercurial ointment. For seborrheic keratoses that have become malignant, Dr. Sutton recommends radical excision. Radium and Roentgen rays are the treatment of choice on the face in the nasal and orbital regions. If Dr. Sutton would have had access to the present invention, his toxic methods utilizing mercury would not have been necessary.

High-frequency electrosurgery has provided dermatology and other areas of medicine with an efficient means of tissue destruction and hemostatis which has been used for seborrheic keratosis removal. When electrosurgery is used for seborrheic keratosis removal, little attention is given to risks of contamination. Indirect contamination can occur as a result of the aerosolization of blood droplets secondary to mechanical actions at the high-frequency electrosurgery site. Hepatitis B or human immunodeficiency disease might be spread through aerosolized microdroplets of blood and electrosurgical smoke.

Electrocoagulation incorporates the patient himself into the electrical circuit with the use of a dispersive electrode plate. This dispersive electrode plate allows the machine to deliver a larger amount of current to the patient. Electrocoagulation occurs when electrosurgical current is applied to the tissue with resistance (ohmic) heat production that cooks tissue. The cooked tissue produces aerosolized microdroplets of blood and electrosurgical smoke. The mechanical action of electrosurgical current entering tissue can give rise to very small blood droplets that can travel a great distance. These droplets get scattered all about the surgical field. Of further concern is the problem of the microdroplets that cannot be seen but may be inhaled or received through the conjunctival surfaces.

Electrodesiccation is the superficial dehydration of tissue as a result of the passage of high-frequency current which leads to scarring and hypopigmentation in some treatments of seborrheic keratosis removal.

Every medical practitioner and dermatologist who practices high-frequency electrosurgery should provide surgical masks and eye protection to everyone in the premises and sterilize all exposed surfaces.

The smoke generated by laser surgery is capable of carrying viable viral particles. Seborrheic keratosis elimination attempts with various lasers commonly used in dermatology such as the carbon dioxide, erbium:YAG, and ND:YAG have been so disappointing that the treatment often leaves a worse cosmetic result than the seborrheic keratosis consisted of.

Cryosurgery of seborrheic keratoses with liquid nitrogen and carbon dioxide has been found to cause dischromic patches due to freezing of the skin surrounding the margin of the lesion. Recovery of the patient takes up to three weeks versus no recovery time using the present invention.

Seborrheic keratoses are the leading cause of visits to dermatologists according to Henry H. Roenigk, Jr. M. D., a leading dermatologist with the Mayo Clinic in Scottsdale, Ariz. Dr. Roenigk generally discourages seborrheic keratosis treatment of any type unless trauma or malignancy of the seborrheic keratosis is present.

Medical practitioners such as dermatologists, plastic surgeons and general practitioners are extremely reluctant to treat facial seborrheic keratoses with current methods because of the high incidence of lawsuits due to unsatisfactory results such as scarring, hyperpigmentation and hypopigmentation.

Twenty five dermatologists and medical doctors in metropolitan practice were surveyed as to seborrheic keratosis removal method, side effects, pricing, insurance reimbursement, and appointment lead time. Fifty-two percent of the dermatologists surveyed used the inject, cut, burn, and bandage method of seborrheic keratosis removal with no form of seborrheic keratosis prevention. All of the dermatologists and medical doctors surveyed reported scarring after their particular type of treatment. None of the dermatologists or medical doctors surveyed reported using any type of topical treatment, clearly pointing to the need for the present invention of seborrheic keratosis elimination.

SUMMARY OF THE INVENTION

The present invention overcomes the drawbacks in the art by providing improved treatments for the safe, effective treatment, elimination, and prevention of seborrheic keratoses anywhere on the patient, including but not limited to the eyelids, groin and axillae.

In another aspect of the present invention, a seborrheic keratosis treatment composition is provided which can be applied by a dermatologist, physician, plastic surgeon, medical ancillary personnel, and an aesthetician, as well as by the patient using at-home products. It may be applied using any suitable means, such as by brush, dropper, atomizer, injector, sprayer, occlusive patch or pipette.

In accordance with the present invention, various reactive oxygen species and oxidative compositions are employed to elicit necrogenous oxidation and oxygen induced apoptosis of cells in the seborrheic keratoses with oxygenation normalization of adjacent cells.

In accordance with the present invention, a seborrheic keratosis composition is provided which can be used to treat any type and location of the specific seborrheic keratosis.

In one aspect of the invention, the seborrheic keratosis treatment compositions are comprised of reactive oxygen species, such as the hydrogen peroxide, superoxide anion, and hydroxyl radicals. In particular, hydrogen peroxide in a concentration far above levels encountered in mammalian metabolism is applied until the offending seborrheic keratosis is eliminated from the skin.

In another aspect of the invention, a method is provided for the treatment of seborrheic keratosis comprising: (a) obtaining a composition comprising hydrogen peroxide in a concentration of at least 23 percent; (b) and applying said composition to an acrochordon on an seborrheic keratosis afflicted person or animal, including domesticated animals. In certain embodiments of the invention, a concentration of hydrogen peroxide used may be least 23, 24, 27, 30, 35, 40, 43, 48, 50, 55, 60, 65, 70, 75 or at least 80 percent and may also be from about 23 percent to about 80 percent; from about 35 percent to about 60 percent; from about 35 percent to about 40 percent, from about 40 percent to about 50 percent, from about 43 percent to about 48 percent, and from about 60 to about 80 percent.

The composition may also include various organic solvents, amino acids, vitamins, organic and/or inorganic minerals; alpha hydroxy, beta hydroxy, carboxylic or keto acids, hormones, enzymes, coenzymes, botanical actives and/or organic oxides and reductants.

In another aspect of the invention, a composition used in accordance with the methods of the invention may comprise ingredients in addition to hydrogen peroxide, for example, at least one vitamin. In one embodiment of the invention, the vitamin is selected from the group consisting of ascorbic acid, niacin, thiamin and riboflavin and may also be L-ascorbic acid.

In another aspect of the present invention, the composition may also comprise at least one amino acid, including, for example, tyrosine, phenylalanine, carnitine, arginine, glycine, alanine, valine, leucine, isoleucine, serine, threonine, cysteine, cystine, methionine, asparagine, glutamine, lysine, 5-hydroxylysine, histidine, tryptophan, proline, ornithine, and carnosine. In one embodiment of the invention, the amino acid is L-carnitine.

In another aspect of the invention, a composition used in accordance with the methods of the invention may comprise at least one melanin inhibitor. Examples of such melanin inhibitors include hydroquinone, niacinimide, cinnamic acid, gamma-L-glutamyl-L-cystine, gamma-L-cysteine, oxidized glutathione, phenol, polyphenol, linoleic acid, ellagic acid, glycyrrhizic acid, alkylsalicylic acid, kojic acid, kojic acid glycosides, kojic acid succinimide ester, kojic acid dimer, thiazoles, propionic acid, sulphur, kudzu root, lavanol, caffeic acid, dicaffeoylquinic acid, tricaffeoylquinic acid, vitamin K, hydantoin, tranexamic acid, chromone derivative, indomethicin methacin, erthorbic acid, glucoside, conchiolin hydrolyzate, licorice root extract, logwood extract, gromwell seed extract, arbutin, chitosan, superoxide dismutase, melanostatin, S-lactoyl glutathione, and hydroquinone glycoside. Other melanin inhibitors include azelaic acid, bearberry extract, bilberry extract, rumex crispus, magnesium ascorbyl phosphate, ascorbyl palmitate, phytic acid, and niacinamide. In one embodiment of the invention the melanin inhibitor is kojic acid.

In still yet another aspect of the invention, a composition used in accordance with the methods of the invention may comprise at least one organic acid. Examples of such an organic acid include lactic acid, citric acid, isocitric acid, glycolic acid, malic acid, tartronic acid, tartaric acid, glucoronic acid, pyruvic acid, acetyl pyruvic acid, β-fluoropyruvic acid, 2-hydroxy isobutyric acid, galacturonic acid, salicylic acid, succinic acid, mandelic acid, β-phenyllactic acid, saccharic acid, β-phenylpyruvic acid, α-hydroxybutyric acid, α-hydroxyisobutyric acid, mucic acid, atrolactic acid, glucoheptonic acid, gluconic acid, glyceric acid, quinic acid, glyceruric acid, threuric acid, erythreuric acid, xyluric acid, lyxuric acid, arabinuric acid, riburic acid, iduric acid, guluric acid, mannuric acid, altruric acid, alluric acid, taluric acid, xylaric acid, lyxaric acid, trihydroxybutanoic acid, pentahydroxyhexanoic acid, hexahydroxyheptanoic acid, and phytic acid. In one embodiment of the invention, the organic acid is L-lactic acid.

In still yet another aspect of the invention, a composition used in accordance with the methods of the invention may comprise at least one hormone. Examples of such hormones include dehydroepiandrosterone, progesterone, estrogen, melatonin, testosterone, pregnenolone, thyroid hormone, thymus hormone, human growth hormone and melatonin. In one embodiment, the hormone is melatonin.

A composition used with the invention may also comprise at least one sulfoxide. Examples of such a sulfoxide include is selected from the group consisting of dimethylsulfoxide and decylmethylsulfoxide. In one embodiment of the invention, the sulfoxide is dimethylsulfoxide.

In still yet another aspect of the invention, a composition used in accordance with the methods of the invention may comprise at least one alcohol, including ethanol, propanol, butanol, pentanol, hexanol, octanol, nonanol, decanol, 2-butanol, 2-pentanol, benzyl alcohol and ethanol. In one embodiment, the alcohol comprises ethanol.

In still another aspect of the present invention, the composition may also comprise at least one fatty acid, including valeric acid, heptanoic acid, pelagonic acid, caproic acid, capric acid, lauric acid, myristic acid, stearic acid, oleic acid, caprylic acid and myristic acid. In one embodiment, the fatty acid comprises myristic acid.

In another aspect of the present invention, the composition may still further comprise at least one fatty acid ester, including isopropyl myristate, isopropyl palmitate, octyldodecyl myristate, ethyl acetate, butyl acetate, methyl acetate, methylvalerate, methylpropionate, diethyl sebacate, and ethyl oleate. In one embodiment, the fatty acid ester is isopropyl palmitate.

In another aspect of the present invention, the composition may also comprise at least one polyol, including propylene glycol, polyethylene glycol, ethylene glycol, diethylene glycol, triethylene glycol, dipropylene glycol, glycerol and propylene glycol. In one embodiment, the composition comprises propylene glycol.

In accordance with the present invention, the composition may also comprise at least one amide, including urea, dimethylacetamide, diethyltoluamide, dimethylformamide, dimethyloctamide, dimethyldecamide, hexamethylenelauramide, diethanolamine, triethanolamine and dimethylformamide. In one embodiment, the amide is dimethylformamide.

In still yet another aspect of the invention, a composition used in accordance with the invention may comprises at least one surfactant, including sodium laurate, sodium lauryl sulphate, cetyltrimethyl ammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride, Poloxamer (231, 182, 184), Brij (30, 93, 96,99), Span (20, 40, 60, 80), Myrj (45, 51, 52), Miglyol 840, sodium cholate, sodium salts of taurocholic, glycolic, desoxycholic acids and lecithin. In one embodiment, the surfactant is lecithin.

In still yet another aspect of the present invention, the composition may also comprise at least one terpene, including D-limonene, α-pinene, β-carene, α-terpineol, terpinen-4-ol, carvol, carvone, pulegone, piperitone, menthone, cyclohexene oxide, limonene oxide, α-pinene oxide, cyclopentene oxide, 1,8-cineole, ylang ylang, anise, chenopodium and eucalyptus. In one embodiment, the terpene is cyclhexene oxide.

In another aspect of the present invention, the composition may also comprise at least one alkanone, including N-heptane, N-octane, N-nonane, N-decane, N-undecane, N-dodecane, N-tridecane, N-tetradecane, and N-hexadecane. In one embodiment, the alkanone is N-octane.

In another aspect of the present invention, the composition may still further comprise aloe vera.

In still yet another aspect of the invention, a composition used in accordance with the invention may comprise at least one gamma linoleic precursor, including borage oil, black currant oil, and evening primrose oil.

In still yet another aspect, the invention provides a method for the removal of seborrheic keratosis comprising: (a) obtaining a composition comprising hydrogen peroxide in a concentration of at least 23 percent and at least one compound selected from the group consisting of a vitamin, an amino acid, a melanin inhibitor, an organic acid, a hormone, a sulfoxide, an alcohol, a fatty acid, a fatty acid ester, a polyol, an amide, a surfactant, a terpene, an alkanone, aloe vera, and a gamma linoleic precursor; and (b) applying said composition to an acrochordon on an seborrheic keratosis afflicted person or domesticated animal.

In certain embodiments of the invention, the concentration of hydrogen peroxide is at least about 23, 24, 27, 30, 35, 40, 43, 48, 50, 55, 60, 65, 70, 75 or at least about 80%, including from about 23 percent to about 60 percent, from about 35 percent to about 60 percent, from about 35 percent to about 40 percent, from about 40 percent to about 50 percent, and from about 43 percent to about 48 percent.

In one embodiment, the composition may additionally comprise kojic acid, dimethylsulfoxide, melatonin, L-ascorbic acid and ethanol; including about at least 26 percent hydrogen peroxide. More particularly, in one embodiment, the composition comprises about 1–5 percent kojic acid, about 10–15 percent dimethylsulfoxide, about 0.1 to 1 percent melatonin, 0.5 to 2 percent L-ascorbic acid and 10–20 percent ethanol.

In another embodiment of the invention, the composition may additionally comprise lactic acid, niacin, testosterone, licorice root extract, and -phenylpyruvic acid. For example, the composition may contain about 47 percent hydrogen peroxide, about 14 percent lactic acid, about 2 percent niacin, about 2 percent testosterone, about 1 percent licorice root extract, and about 0.5 percent β-phenylpyruvic acid. In yet another embodiment of the invention, the composition may additionally comprise L-tyrosine, phenylalanine, tricaffeoylquinic acid and ethanol; including a composition of about 23 percent hydrogen peroxide, about 2 percent L-tyrosine, about 2 percent phenylalanine, about 1 percent tricaffeoylquinic acid, and about 18 percent ethanol.

In the method, the composition may comprise lactic acid, glycolic acid, salicylic acid, citric acid, and ethanol. For example, the invention includes a composition of about 23 percent hydrogen peroxide, about 4 percent lactic acid, about 4 percent glycolic acid, about 4 percent salicylic acid, about 4 percent citric acid, and about 20 percent ethanol. The composition may also comprise dimethysulfoxide; including a composition of about 35 percent hydrogen peroxide and about 35 percent dimethysulfoxide. The composition may still further comprise L-ascorbic acid, niacin, glycine, hydroquinone, superoxide dismutase, galacturonic acid and ethanol; including a composition of about 35 percent hydrogen peroxide, about 0.5 percent L-ascorbic acid, about 0.5 percent niacin, about 0.5 percent glycine, about 0.5 percent hydroquinone, about 0.5 percent superoxide dismutase, about 5 percent galacturonic acid and about 14 percent ethanol. In another embodiment of the invention, the composition may additionally comprise decylmethylsulfoxide; including a composition of about 60 percent hydrogen peroxide and 6 percent decylmethylsulfoxide.

BRIEF DESCRIPTION OF THE DRAWINGS

FIG. 1 is a photograph showing a patient having seborrheic keratosis before treatment in accordance with the present invention.

FIG. 2 is a photograph showing the patient of FIG. 1 after undergoing treatment in accordance with the present invention.

DESCRIPTION OF ILLUSTRATIVE EMBODIMENTS

The present invention provides effective methods for removal and prevention of unsightly and potentially precancerous seborrheic keratoses while avoiding the pain and scarring that accompanies presently known techniques. The inventors have discovered that reactive oxygen species such as the superoxide radical, hydrogen peroxide, hydroxyl radical, singlet oxygen and ozone, as well as other oxidants, are effective in eliminating seborrheic keratoses when applied in sufficient concentration and frequency. The preferred active agents include hydrogen peroxide, benzoyl peroxide, and alloyl peroxide.

One such method of oxidative seborrheic keratosis elimination is providing one or more applications of a composition including unstabilized hydrogen peroxide with a concentration of at least 23 percent. High concentration food grade hydrogen peroxide application results in, surprisingly, the complete removal of seborrheic keratoses, and other unsightly and undesirable skin disorders, without causing scarring, hypopigmentation or hyperpigmentation.

Removal and prevention treatments of the present invention may include components with a high degree of biocompatibility, such as products of mammalian metabolism, components of the electron transport chain and may include hydrogen peroxide, amino acids, vitamins, organic and/or inorganic minerals; alpha hydroxy, beta hydroxy, carboxylic or keto acids, hormones, enzymes, coenzymes and various penetration enhancers. Other components such as botanical actives and/or organic oxides and reductants may also be employed, as is known to those of skill in the art. Such compounds may be contained in a solvent such as water or another solvent compatible with hydrogen peroxide. Further, physiologically acceptable adjuvants may also be chosen, for example, pH-regulating agents, antioxidants, preservatives, pigments and colorings, emollients, antifoams, plant or animal oils or waxes, silicones, perfumes, surfactants, plasticizers, thickening polymers other compounds. Of course, persons skilled in the art will be careful to choose any such optional additional compounds and their quantity so that the active properties of the hydrogen peroxide are not substantially reduced by the addition.

One preferred brand of hydrogen peroxide found to function well is Durox™, manufactured in the Hydrogen Peroxide Division of FMC of Canada Ltd. The methods of the invention involve a sufficient topical application of the oxidative composition directly to the selected seborrheic keratosis. The oxidative composition may be left on the treated seborrheic keratosis without removal and additional applications applied during a treatment.

Another preferred embodiment of the present invention designed for the rapid oxidative elimination of seborrheic keratoses comprises unstabilized 35 percent hydrogen peroxide and ferrous sulphate such as product number F 7002 produced by the Sigma-Aldrich Company of St. Louis, Mo. The inclusion of ferrous sulphate in the oxidative composition produces the highly reactive hydroxyl radical by the Fenton reaction. The Fenton reaction is $H_2O_2 + Fe^{2+} \rightarrow OH \cdot + OH^- + Fe^{3+}$. The hydroxyl radical is the most reactive oxygen radical known to biochemistry. The hydroxyl radicals initiate free radical chain reactions, which produce lipid peroxidation and lysis in the cells of the seborrheic keratoses. Titanium, copper, cobalt and chromium salts in combination with high concentration food grade hydrogen peroxide may also be utilized in hydroxyl radical generating compositions for the destruction of undesirable cutaneous lesions.

Some patients may experience a slight to moderate burning or stinging sensation upon the application of the oxidative composition, particularly when higher concentrations of 35 percent or greater of unstabilized hydrogen peroxide are used. While the composition may be left on without further treatment even when a transient burning or stinging sensation occurs, it may be desirable to further treat the affected area with a neutralizing composition, such as distilled water or a lotion or cream such as pHaze 17 ReBalance™ cream (Physician's Choice of Arizona).

For total removal of the seborrheic keratosis to occur, more than one application of the oxidative composition or compositions to the seborrheic keratosis will sometimes be necessary. It is envisioned that some seborrheic keratoses may be removed upon one application with a composition including unstabilized food grade hydrogen peroxide at higher concentrations, such as about 36 to 55 percent. However, total removal of the seborrheic keratoses, which may be treated with the present methods, will in some cases require several applications of the oxidative compositions described herein over a period of time. The oxidative composition applications may be spaced minutes, hours or days apart. It is preferred that subsequent oxidative composition treatments occur within two or three days of the previous treatment, although they may be as much as a week or two apart. The spacing of the oxidative composition treatments will depend upon such factors as patient sensitivity and type or types of the seborrheic keratoses present on the seborrheic keratosis afflicted individual.

While described in terms of seborrheic keratosis removal, the present invention is also effective in removing other skin conditions such as condyloma accuminatum, corns, fibroepithelial polyps, prurigo nodularis, inverted follicular keratosis, warts, warty dyskeratosis, actinic keratoses, acrochordons, herpes, clear cell acanthoma, acne, rosacea, basal cell carcinoma, squamous cell carcinoma, onychomycosis, hyperpigmentation, rhytides, psoriasis and malignant melanoma.

While the method of the invention is surprisingly and unexpectedly effective using a composition including simply hydrogen peroxide at concentrations above about 23 percent, including at least about 23, 24, 27, 30, 35, 40, 43, 48, 50, 55, 60, 65, 70, 75 or at least 80 percent. As used herein, "percent" means percent by weight (w/w). The compositions for use in the present methods may also include other substances to aid in penetration, to enhance skin lightening, to aid in moisturizing or conditioning the skin, as will be known to those of skill in the art in view of the instant disclosure. For example, other ingredients may be added to improve the skin condition or the effectiveness of the compositions. Vitamins may added to the compositions to aid in improving the skin condition thereby inhibiting the production of subsequent cutaneous anomalies after treatment of the original condition Case histories of patients who have had various types of lesions successfully removed using the methods of the invention are provided below. These case histories and the examples that follow are included simply for illustration of the effectiveness of the invention and are not meant to limit the scope of the invention in any way.

Case Histories

Case History Number 1

A forty-five year old Caucasian male marathoner with an irritated seborrheic keratosis on the iliotibial band near the left knee did not want to undergo conventional destructive seborrheic keratosis removal methods and suffer downtime during the marathon season. Nor did the marathoner want the scarring and hyperpigmentation or hypopigmentation that results from conventional techniques. The present invention was applied drop by drop to the irritated seborrheic keratosis for five consecutive days. The seborrheic keratosis was dark brown with a hard, shiny surface that resisted composition penetration on the first four applications. A drop of the 35 percent hydrogen peroxide seborrheic keratosis composition was allowed to stand on the lesion for approximately 2 minutes on each of the first four applications. On the fifth application of the seborrheic keratosis composition to the offending lesion a vigorous bubbling reaction occurred as the composition penetrated the dense previously non-porous surface of the seborrheic keratosis. The marathoner reported no pain during the treatment reaction, only a sensation of effervescence. The following day, the seborrheic keratosis fell off during the marathoner's pre-training run shower, leaving a very slightly pinkish tone to the healthy underlying skin. The seborrheic keratosis has not returned three years post treatment.

Case History Number 2

A thirty-eight year old single mother of two presented with an unsightly grayish-pink, verrucous seborrheic keratosis covering her right cheek. She was extremely self-conscious of the lesion and kept her long hair over the seborrheic keratosis to conceal it. The lesion was of several years duration and she always declined to have her picture taken with her family during Christmas and other holidays. The subject was one of twelve children. Several of her siblings also carried the seborrheic keratoses although hers was the worst with the exception of one brother with a large dark seborrheic keratosis on his forehead. One of her other brothers had several seborrheic keratoses removed by laser with great expense and poor results. The dermatologists she consulted recommended either surgical or laser removal but could not guarantee scar-free results. The seborrheic keratosis was treated with a 35 percent plus hydrogen peroxide seborrheic keratosis composition of the present invention and allowed to react completely. Four days post treatment, the subject awoke to find the seborrheic keratosis lying on her pillow. She placed the seborrheic keratosis in a ZIP-LOCK® plastic bag and delivered it to the PCA Skin Center® where it was sent off for histologic examination. The subject was overjoyed with the result of her treatment that left no sign of the seborrheic keratosis. The subject is still keratosis free three years post treatment.

Case History Number 3

An unemployed 36-year-old Caucasian male musician on disability with a history of severe depression and disassociative psychosis presented with a stucco type dark brown seborrheic keratosis of long duration on the right side of his forehead. He also carried smaller seborrheic keratoses scattered about his face, chest and legs. Several acrochordons were present on both sides of neck. The large seborrheic keratosis measured 2.5×3 centimeters in diameter and was raised about 2.5 millimeters.

The pretreatment interview revealed the man was heavily medicated daily with eleven prescriptions drugs for control of his mental condition and depression. His diet consisted of a favorite brand of TV dinner with continuous coffee consumption and cigarette chain smoking. He admitted to performing no daily exercise whatsoever.

Out of twelve children in his family, the majority had at least one seborrheic keratosis of some type with several family members afflicted with multiple seborrheic keratoses. He was referred for treatment by his older sister who had a large disfiguring seborrheic keratosis on her right cheek, which had been successfully treated with the present invention. He had been discouraged from treatment with conventional methods of seborrheic keratosis treatment by the results obtained from other family members who had experienced pain, scarring, hyperpigmentation and great expense. His brother, a prominent Hollywood movie director, had laser removal of facial seborrheic keratoses at a cost of several thousand dollars. The laser treatment resulted in facial scarring and hyperpigmentation with a great deal of discomfort both during the procedure and post treatment.

Extensive photographic documentation was performed pre and post treatment to chart treatment progress. The seborrheic keratosis removal composition of high concentration peroxide of hydrogen was applied to the seborrheic keratoses and allowed to react completely with little or no discomfort. The acrochordons present on both sides of the neck were treated with the hydrogen peroxide acrochordon composition.

The second seborrheic keratosis treatment was performed one week later. Several of the smaller seborrheic keratoses had avulsed and the remainder appeared soon to avulse. The large seborrheic keratosis on the forehead exhibited detachment around the outer margin of the lesion.

The acrochordons on the neck had depedunculated and the smaller facial seborrheic keratoses had fallen off at the time of the third treatment with no scarring or pigmentation anomalies. The large forehead seborrheic keratosis showed further signs of detachment. The seborrheic keratoses typically develop an oxidized scale which flakes or comes off in various size fragments.

Two days prior to the fourth seborrheic keratosis treatment, the large 2.5×3 centimeter seborrheic keratosis on the forehead fell off while the subject was taking a shower. A slight seborrheic keratosis remnant and very slight darker pigmentation were visible upon close examination. The musician was very pleased with the results of the treatment.

Further appointments were scheduled to apply the seborrheic keratosis prevention composition to eliminate newly forming seborrheic keratoses. Superficial skin peels of the modified Jessner's type were performed at later dates to freshen the skin and even out the skin tone where the seborrheic keratoses were removed.

Follow up visits at three and six months, revealed a dramatically improved overall facial skin appearance with no visible evidence of the prior seborrheic keratoses. The subject exhibited a marked improvement in self-image to correspond with his improved facial skin appearance. The musician has since returned to performing music without embarrassment of being on stage because of the disfiguring seborrheic keratoses.

Case History Number 4

A forty-eight year old Caucasian woman of English and French descent presented with multiple brownish scaly seborrheic keratoses of the verrucous type scattered across her entire back. The seborrheic keratoses varied in size to a maximum of 2.7 centimeters. In contrast to the stucco type keratoses, the lesions were subsurface to the epidermis as if they were eroding away the skin.

The subject had a history of heavy consistent antibiotic use and multiple allergies before a recent conversion to natural medicine. Her seborrheic keratoses growth began after a severe antibiotic reaction, which required hospitalization.

A thirty-five percent hydrogen peroxide seborrheic keratosis treatment composition was applied to the lesions after the border of the seborrheic keratoses had been surrounded by the protective pHaze 17 ReBalance™ cream to contain the solution within the area of the lesions.

Lesion blanching was observed after an average of 48 seconds, on the majority of the larger seborrheic keratoses and the subject reported a moderate stinging sensation for several minutes. The majority of the smaller seborrheic keratoses disappeared after the initial treatment and the larger seborrheic keratoses required 3 to 4 treatments at roughly one-week intervals to obtain complete resolution.

Case History Number 5

A one centimeter diameter verrucous, pseudohorncystic seborrheic keratosis on the left jaw anterior to the ear lobe prompted the 53 year old Caucasian female to seek treatment with the current invention. Her family physician had referred her to a dermatologist who informed her surgical or laser removal would result in scarring.

Initial application of the seborrheic keratosis removal composition caused the irritated seborrheic keratosis to fall off prior to the second treatment. The very slight remainder of the irritated seborrheic keratosis was treated to achieve complete resolution with no scarring, bleeding or pigmentation anomalies.

Seborrheic Keratosis Study Results

Thirty-two subjects afflicted with various types of seborrheic keratoses, acrochordons and other benign epidermal proliferations were recruited, screened and enrolled in a one year study to test the effects of the present invention. The Human Welfare Committee at Arizona State University in Tempe, Ariz. granted Institutional Review Board approval to conduct a double blind vehicle controlled study of the effect of the present invention with active ingredient versus its vehicle only in the treatment of benign epidermal proliferations: seborrheic keratoses, benign keratoses, verruca and others at one year. More than ample study participant candidates were obtained by one small ad in a small local newspaper. In most instances, it was almost impossible to tell where the seborrheic keratoses had been after treatment was completed. On a few subjects, especially those with darkly pigmented seborrheic keratoses and fair skin, a faint pinkish coloration remained after treatment that appears to be fading over time. The procedure was well tolerated by all subjects except two who displayed unusual sensitivity and requested premature application of the neutralizing composition. Most of the seborrheic keratosis carriers treated have shown no sign of seborrheic keratosis re-growth.

More specifically, a total of 32 patients were initially enrolled in this study. These were comprised of 12 men and 20 women, having an average age of 53. During the study, 10 patients were lost to follow-up. Three patient failed to return after their initial visit, and were lost to follow-up, despite multiple attempts to contact them. Therefore, this left a total of 19 active data points and 19 placebo data points at three months. At three months, these patients had received, on average, 6 applications of the PCS-01 formulation to their lesions.

All viable data was then analyzed, first using a Shapiro-Wilk evaluation for continuous summary descriptives. The mean number of benign epidermal proliferations remaining at Day 0 at actively treated sites was 29 (SE 5.5404), while the mean number of benign epidermal proliferations remaining for placebo treated sites at Day 0 was 23 (SE 4.4663). The mean number of benign epidermal proliferations remaining at Day 90 at actively treated sites was two (SE 0.5299), while the mean number of benign epidermal proliferations remaining for placebo treated sites at Day 90 was 23 (SE 4.4642). This was statistically significant in a paired samples t-test of active versus placebo at Day 90 (p-value<0.0001). Again, these analyses were done using paired sample, two tailed t-tests This data is summarized in tabular form below:

| Day 0 - Treated Patients | |
|---|---|
| n | 20 (cases excluded: 3 due to missing value) |
| Mean | 28.650 |
| 95% Cl | 17.054 to 40.246 |
| Variance | 613.9237 |
| SD | 24.775 |

| Day 0 - Treated Patients | |
|---|---|
| SE | 5.5404 |
| CV | 86% |
| Median | 23.000 |
| 95.9% Cl | 7.000 to 36.000 |
| Range | 81 |
| IQR | 42.25 |
| Percentile | |
| 2.5th | — |
| 25th | 6.500 |
| 50th | 23.000 |
| 75th | 48.750 |
| 97.5th | — |

| Day 0 - Untreated Patients | |
|---|---|
| n | 20 (cases excluded: 3 due to missing value) |
| Mean | 23.373 |
| 95% Cl | 14.025 to 32.721 |
| Variance | 398.9538 |
| SD | 19.9738 |
| SE | 4.4663 |
| CV | 85% |
| Median | 25.000 |
| 95.9% Cl | 7.000 to 31.000 |
| Range | 65 |
| IQR | 29.75 |
| Percentile | |
| 2.5th | — |
| 25th | 6.500 |
| 50th | 25.000 |
| 75th | 36.250 |
| 97.5th | — |

| Day 90 - Treated Patients | |
|---|---|
| n | 20 (cases excluded: 3 due to missing value) |
| Mean | 1.396 |
| 95% Cl | 0.287 to 2.5056 |
| Variance | 5.6165 |
| SD | 2.3699 |
| SE | 0.5299 |
| CV | 170% |
| Median | 0.000 |
| 95.9% Cl | 0.000 to 1.923 |
| Range | 8 |
| IQR | 2.730769231 |
| Percentile | |
| 2.5th | — |
| 25th | 0.000 |
| 50th | 0.000 |
| 75th | 2.731 |
| 97.5th | — |

| Day 90 - Untreated Patients | |
|---|---|
| n | 20 (cases excluded: 3 due to missing value) |
| Mean | 23.319 |
| 95% Cl | 13.975 to 32.663 |
| Variance | 398.5888 |
| SD | 19.9647 |
| SE | 4.4642 |
| CV | 86% |
| Median | 24.500 |
| 95.9% Cl | 7.000 to 31.000 |
| Range | 65 |
| IQR | 29.75 |
| Percentile | |
| 2.5th | — |
| 25th | 6.500 |
| 50th | 24.500 |
| 75th | 36.250 |
| 97.5th | — |

No adverse events directly attributable to the formulation of the present invention were found during this phase of the study. When the formulation was applied, the patients noted a transient, less than 10 minute burning following application of formulation of the present invention. On a discomfort scale, with 1 being no discomfort and 10 being maximal discomfort, the patients average rating was a 2.5.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Acanthotic Seborrheic Keratosis Removal

The following is a general procedure or method for application of the selected agents and compositions for the removal of acanthotic seborrheic keratoses:

a. complete medical history form and discuss procedure with the seborrheic keratoses afflicted individual;

b. conduct full body examination to locate any various seborrheic keratoses overlooked by afflicted person and detect any newly-forming seborrheic keratoses;

c. photograph seborrheic keratoses, preferably with 1×, 30× and 50× magnification;

d. cleanse seborrheic keratoses with pHaze 1 Facial Wash™ (Physician's Choice of Arizona) cleansing composition;

e. apply neutralizer composition to the skin surrounding seborrheic keratosis;

f. apply 50 percent hydrogen peroxide acanthotic seborrheic keratosis composition with appropriate application instrument (e.g., a brush);

g. accelerate drying with miniature heated forced air dryer;

h. watch for appearance of blanching and bubbling reaction;

i. make second application of acanthotic seborrheic keratosis composition if necessary;

j. photograph seborrheic keratoses, preferably with 1×, 30× and 50× magnification;

k. supply seborrheic keratosis afflicted person with pHaze 17 ReBalance™ cream for application eight hours post seborrheic keratosis treatment;

l. inform carrier that seborrheic keratoses should spontaneously detach 3 to 6 days after procedure;

m. re-apply pHaze 17 ReBalance™ cream to seborrheic keratosis skin attachment site after seborrheic keratosis detaches;

n. check at weekly intervals to ensure re-growth does not occur.

EXAMPLE 2

Hyperkeratotic Seborrheic Keratosis Removal

The following is a general method for the alleviation of the dome-shaped papules known as hyperkeratotic seborrheic keratoses, which usually involve the trunk and lower extremities:

a. complete medical history form and discuss procedure with the hyperkeratotic seborrheic keratosis afflicted individual;

b. conduct full body examination to locate all hyperkeratotic seborrheic keratoses;

c. photograph hyperkeratotic seborrheic keratoses, preferably with 1×, 30× and 50× magnification;

d. cleanse hyperkeratotic seborrheic keratoses with pHaze 1 Facial Wash™ cleansing composition;

e. apply pHaze 17 ReBalance™ cream to skin surrounding hyperkeratotic seborrheic keratoses;

f. apply hyperkeratotic seborrheic keratosis induction formulation containing 45 percent hydrogen peroxide;

g. accelerate evaporation with heated forced air dryer;

h. watch for appearance of blanching and bubbling reaction;

i. make second application of hyperkeratotic seborrheic keratoses apoptotic induction formulation, if necessary, to achieve complete penetration;

j. photograph hyperkeratotic seborrheic keratoses, preferably with 1×, 30× and 50× magnification;

k. supply hyperkeratotic seborrheic keratosis afflicted individual with pHaze 17 ReBalance™ cream for application eight hours post apoptotic induction treatment;

l. inform hyperkeratotic seborrheic keratosis afflicted individual that apoptotic crust should form after one day and crust should separate after approximately 3 days;

m. re-apply pHaze 17 ReBalance™ cream to hyperkeratotic seborrheic keratoses lesions after crust separation;

n. re-treat hyperkeratotic seborrheic keratoses two days after crust separation until satisfactory elimination of lesions is achieved.

EXAMPLE 3

Dermatolipoma Seborrheic Keratosis Removal

Type III fat filled acrochordon seborrheic keratosis variants known as dermatolipoma acrochordons require a modified procedure and a specialized depedunculation formulation application such as the following:

a. complete medical history form and discuss procedure with the dermatolipoma acrochordon afflicted individual;

b. conduct full body examination to locate all dermatolipoma seborrheic keratoses;

c. perform photographic documentation at specified magnifications;

d. dehydrate dermatolipoma surface with heated air blower;

e. apply dermatolipoma 35 percent hydrogen peroxide depedunculation formulation;

f. monitor reaction and reapply to achieve thorough lesion blanching;

g. re-treat dermatolipomas that do not depedunculate 5 days post initial treatment.

EXAMPLE 4

Verrucous Seborrheic Keratosis Treatment

The following general procedure should be utilized for the treatment of verrucous seborrheic keratoses with diffuse parakeratosis and absence of the granular layer:

a. complete medical history form and discuss procedure with the verrucous seborrheic keratosis carrier;

b. conduct photographic documentation;

c. layer two applications of the 38 percent hydrogen peroxide formulation to the verrucous seborrheic keratoses;

d. treat the verrucous seborrheic keratoses with the A&C Synergy Serum™ (Physician's Choice of Arizona) one day post treatment;

e. retreat any unresolved verrucous seborrheic keratoses at 5 day intervals.

EXAMPLE 5

Seborrheic Keratosis Prevention Treatment

The following seborrheic keratosis prevention treatment should be adjusted depending on individual skin sensitivity and propensity for seborrheic keratosis proliferation:

a. fill a bath tub with moderately warm water;

b. add the container of the 35 percent hydrogen peroxide solution to the bath water;

c. soak in the tub with the seborrheic keratosis prevention solution for at least fifteen minutes;

d. repeat the treatment at weekly intervals;

e. treat any existing seborrheic keratoses with the concentrated seborrheic keratosis solution.

EXAMPLE 6

Clear Cell Acanthoma Treatment a. complete medical history form and discuss clear cell acanthoma treatment with the subject;

b. conduct full body examination to locate all lesions to be treated and categorize lesion types;

c. perform photographic documentation at various magnifications;

d. pHaze 17 ReBalance™ cream to surround clear cell acanthoma;

e. apply 45 percent hydrogen peroxide solution to achieve saturation of each clear cell acanthoma;

f. check for resolution of lesions 5 days post treatment.

Exemplary compositions in accordance with the present invention include:

EXAMPLE A

Hydrogen peroxide (at least 23%)
Witch hazel
Aloe vera
Lactic acid, about 2 to 10%, preferably about 5%
Citric acid, about 2 to 10%, preferably about 5%
Water

EXAMPLE B

Hydrogen peroxide (at least 23%)
Aminoguanidine 0.1 to 5%, preferably about 1%
Lactic acid, about 2 to 10%, preferably about 5%
Citric acid, about 2 to 10%, preferably about 5%
Water

EXAMPLE C

Hydrogen peroxide (at least 23%)
L-ascorbic acid, about 5% to 10%
L-arbutin
Kojic acid
Hydroqinone
Lactic acid
Licorice root extract
Retinol
Water

EXAMPLE D

Hydrogen peroxide (at least 23%)
L-ascorbic acid, about 5% to 10%
Methyl sulfonyl methane (MSM)
Sodium hyaluronate
Water

EXAMPLE E

Hydrogen peroxide (at least 23%)
Azelaic acid
Glucosamine
Niacinamide
Witch hazel
Water Since specific individual seborrheic keratosis type and conditions may warrant changes and modifications of the present seborrheic keratosis removal and prevention invention and can readily be made by those skilled in the art of seborrheic keratosis removal and prevention without departing from the basic concept of the present invention, the present invention for seborrheic keratosis removal and prevention shall not be limited except by the scope of the appended claims.

All of the treatments and/or methods disclosed and claimed herein can be made and executed without undue experimentation in light of the present disclosure. While the treatments and methods of this invention have been described in terms of preferred embodiments, it will be apparent to those of skill in the art that variations may be applied to the treatments and/or methods and in the steps or in the sequence of steps of the method described herein without departing from the concept, spirit and scope of the invention. More specifically, it will be apparent that certain seborrheic keratosis removal and prevention agents which are both chemically and physiologically related may be substituted for the agents described herein while the same or similar results would be achieved. All such similar substitutes and modifications apparent to those skilled in the art of seborrheic removal and prevention are deemed to be within the spirit, scope and concept of the invention as defined by the appended claims.

REFERENCES

The following references, to the extent that they provide exemplary procedural or other details supplementary to those set forth herein, are specifically incorporated herein by reference:

U.S. Patents
U.S. Pat. No. 3,949,072, April, 1976 to Tenta
U.S. Pat. No. 3,954,974, May, 1976 to Herzog
U.S. Pat. No. 4,112,121, September, 1978 to Tenta
U.S. Pat. No. 4,384,000, May, 1983 to Lanier
U.S. Pat. No. 4,438,102, March, 1984 to Ganci
U.S. Pat. No. 4,485,091, November, 1984 to Fitton
U.S. Pat. No. 4,826,681, May 1989, to Jaquet, et al.
U.S. Pat. No. 5,164,394, November, 1992 to Bolund
U.S. Pat. No. 5,200,170, April, 1993 to McDow
U.S. Pat. No. 5,380,764, January, 1995 to Herzog
U.S. Pat. No. 5,376,582, April 1998 to Devillez
U.S. Pat. No. 5,420,114, May, 1995 to Clodman
U.S. Pat. No. 5,958,984, September, 1999 to Devillez
U.S. Pat. No. 5,981,586, November, 1999 to Pershadsingh
U.S. Pat. No. 6,036,684, March, 2000 to Tankovich
U.S. Pat. No. 6,171,593, January, 2001 to Williams
Other Publications
Books
Allen, A. C.: *The Skin* Mosby, St. Louis; page 704; 1954.
Arndt, K. A.: *Manual of Dermatologic Therapeutics*, Little Brown & Co., Inc.; Boston, Mass.; pages 106–109; 1989.
Caro, W. A.; Bronstein, B. R.: Tumors of the Skin. In: Moschella, S. L.; Hurley, H. J. (eds.): *Dermatology*, $2^{nd}$ edn.: W. B. Saunders Co.; 1533–1638; 1985.
Fitzpartirck, Thomas B.; Eisen, Arthur Z.; Wolff Klas; Freedurg, Irwin M.; and Austen, K. Frank, editors. In: *Dermatology in General Medicine*, 3th edition, New York: McGraw-Hill, page 1036; 1991.
Goldsmith, L. A.: In: *Biochemistry and Physiology of the Skin*, vol. I–II; Oxford University Press; pages - ; 1983.
Graham-Brown, R.; Burns, T.: Benign and Malignant Skin Tumors. In: *Lecture Notes on Dermatology* $7^{th}$ edition, Oxford UK: Blackwell Science Ltd., pages 121–123; 1996.
Gray, H. R.: In: Graham, J. H.; Johnson, W. C.; Helwig, E. B. (eds.): *Seborrheic Keratosis in Dermal Pathology*, Harper & Row; Hagerstown, Md.; page 538; 1972.
Ho, V. C. Y.; McLean, D. I.: Benign Epithelial Tumors: In: Fitzpatrick, T. B.; Eisen, A. Z.; Wolff, K.; Freedberg, I. M.; Austen, K. F. (eds.): *Dermatology in General Medicine*, $4^{th}$ edn.; McGraw-Hill; New York; pages 855–872; 1993.
King, L. E.; Stoscheck, C. M.; Gates, R.; and Nanney, L. B.: Epidermal growth factor and related growth factors. In: Goldsmith, Lowell A. editor. *Biochemistry and Physiology of the Skin*. New York: Oxford University Press, pages 329–350; 1991.
Kirkham, N.: Seborrheic Keratosis. In: Elder D.; Elenitsas R.; Jaworski, C.; Johnson, B. (eds.): In: *Lever's Histopathology of the Skin*, $8^{th}$ edn.; Lippincott-Raven Publishers; pages 689–693; 1997.
Lever, W. F.; Schuaumburg-Lever, G.: *Histopathology of the Skin*, $7^{th}$ edn., J. B. Lippincott; Philadelphia; pages 528–532; 1990.
Lever, W. F.; Schuaumberg-Lever, G.: *Histopathology of the Skin*, $6^{th}$ edn. J. B. Lippincott; Philadelphia; page 478; page 497; 1983.
Lever, W. F.; Schuaumburg-Lever, G.: *Histopathology of the Skin*, $5^{th}$ edn.; J. B. Lippincott; Philadelphia; page 450; page 454; page 457; pages 522–523; 1975.
Lever, W. F.: *Histopathology of the Skin*, $3^{rd}$ edn.; J. B. Lippincott, Philadelphia, pages 412–414; 1961.

Mackie, R. M.: Seborrheic Keratosis: In: Champion, R. H.; Burton, J. L.; Ebling, F. J. G. (eds.): *Textbook of Dermatology* 5$^{th}$ edn. Blackwell Scientific Publications; Oxford, pages 1465–1467; 1992.

Macleod, J. M. H.: *Practical Handbook of the Pathology of the Skin*. London: H. K. Lewis, 91, 132; 1903.

McKee, P. H.: Seborrheic Keratoses. In: McKee, P. H. (ed.): *Pathology of the Skin*, Lippincott; Philadelphia; pages 1424–1426; 1990.

Menzies, S. W.; Crotty, K. A.; Invar, W. H.: *An Atlas of Surface Microscopy of Pigmented Skin Lesions*, McGraw-Hill Book Co.; New York, N.Y.; 1996.

Mier, P. D.: *The Molecular Biology of the Skin*, Blackwell; Oxford; page 127; 1976.

Montgomery, H.: *Dermatopathology*, Harper & Row, Publishers, Inc.; vol. II; page 873; page 879; 1967.

Moshella, S. L.; Pillsbury, D. M.; Hurley, H. J.: In. *Dermatology*, W. B. Saunders & Co.; vol. II; pages 1325–1327; 1975.

Okum, M. R.; Edelstein, L. M.: In: *Gross and Microscopic Pathology of the Skin*, Dermatopathology Foundation Press; pages 570–579; pages 692–693; 1976.

O'Quinn, S.: In: Denis, D. J.; Dobson, R. L.; McGuire, J.: *Seborrheic Keratosis in Clinical Dermatology*, Harper & Row; New York; vol. 4; page 21–1:1; 1974.

Pinkus, H.; Mehregan, A. H.: In: *A Guide to Dermatohistopathology*, 2$^{nd}$ edn.; Appleton-Century-Crofts, New York; page 62; page 484; 1976.

Sanderson, K. V.: Tumours of the Skin. In: Rook, A.; Wilkinson, D. S.; Ebling, F. J. G. (eds.): *Textbook of Dermatology* 2$^{nd}$ edn.; vol. 2, page 1923.

Schwartz, R. A.: The Sign of Leser-Trélat. In: Demis D. J. (ed.). *Clinical Dermatology*, 13$^{th}$ ed.; J. B. Lippincott; Philadelphia; Unit 12–26A: pages 1–3; 1987.

Steffen, C. S.; Ackerman, A. B.: Seborrheic keratosis with Sebaceous Differentiation. In: *Neoplasms with Sebaceous Differentiation*, Lee and Febiger: Philadelphia, 433–457; 1994.

Stewart, W. D.; Danto, J. L.; Maddin, S.: Seborrheic Keratosis. In: *Dermatology-Diagnosis and Treatment of Cutaneous Disorders*, 4$^{th}$ edn.; C. V. Mosby, St. Louis; page 508; 1978.

Stolz, W.; Braun-Falco, O.; Bilek, P.; Landthaler, M.; Cognetta, A. B.: *Color Atlas of Dermatoscopy*, Blackwell Science Ltd.; London, England; 1994.

Sutton, R. L. and Sutton, R. L., Jr.: *Diseases of the Skin*, edn. X; C. V. Mosby Company; 1939.

Wilson, E.: Developmental and Nutritive Affections. In: *Diseases of the Skin* 7$^{th}$ edition, Philadelphia, 328–329; 1868.

Journal Articles

Anderson, P. J.; Zuk, J. A.; and Berry, R. B.: Squamous Cell Carcinoma Arising within Seborrheic Keratosis (Case Report). *Plastic and Reconstructive Surgery* 102(2): 453–455; 1998.

Arons, Marvin S.; and Salomon, Jeffrey C.: Squamous Cell Carcinoma Arising within Seborrheic Keratosis (Discussion). *Plastic and Reconstructive Surgery* 102(2): 456–458; 1998.

Baer, Rudolf L.: Papillated Squamous Cell Carcinoma In Situ Arising in a Seborrheic Keratosis. *Journal of the American Academy of Dermatology* 5: 561–565; 1981.

Baer, Rudolf L.: Giant Pedunculated Seborrheic Keratosis. *Archives of Dermatology* 115: 627; 1979.

Becker, S. W.: Benign Epidermal Neoplasms. *Archives of Dermatology and* 26: 838- ; 1932.

Bilotta, Jeffrey; and Waye, Jerome D.: Hydrogen Peroxide Enteritis: the "Snow White" Sign. *Gastrointestinal Endoscopy* 35: 428–430; 1989.

Bloch, Peter H.: Transformation of Seborrheic Keratosis into Bowen's Disease. *Journal of Cutaneous Pathology* 5: 361–367; 1978.

Caro, Marcus Rayner; and Szmanski, Frederick J.: Seborrheic and Senile Keratoses. *Medical Clinics of North America* 35: 419–431; 1951.

Cascajo, Carlos Diaz; Reichel, Martin; and Sánchez, Jorge L.: Malignant Neoplasms Associated with Seborrheic Keratoses: Analysis of 54 Cases. *The American Journal of Dermatopathology* 18(3): 278–282; 1996.

Cashmore, Robert W.; and Perry, Harold O.: Differentiating Seborrheic Keratosis from Skin Neoplasm. *Geriatrics* 40: 69–75; 1985.

Christensen, David W.; Faught, William E.; Black, Richard E.; Woodward, George A.; and Timmons, Otwell D.: Fatal Oxygen Embolization after Hydrogen Peroxide Ingestion. *Critical Care Medicine* 20(4): 543–544; 1992.

Danis, Richard K.; and Brodeur, Armand E.: The Danger of Hydrogen Peroxide as a Colonic Irrigating Solution. *Journal of Pediatric Surgery* 2(2): 131–133; 1967.

Di Benedetto, Giovanni; Pierangeli, Marina; and Bertani, Aldo: A Peculiar Case of Multiple Gigantic Seborrheic Keratosis. *Plastic and Reconstructive Surgery* 99(5): 1466–1467; 1997.

Di Benedetto, Giovanni; Pierangeli, Marina; and Bertani, Aldo: A Peculiar Case of Multiple Gigantic Seborrheic Keratosis (Letter). *Plastic and Reconstructive Surgery* 101(2): 547; 1998.

Exposures Reported to a Regional Poison Control Center. *Clinical Toxicology* 32(6): 705–714; 1994.

Doll, Donald C.; McCagh, Michael F.; And Welton, William A.: Sigh of Leser-Trélat. *Journal of the American Medical Association* 238(3): 236–237; 1977.

Eads, Thomas J.; Hood, Antoinette F.; Chuang, Tsu-Yi; Faust, Holly B.; and Farmer, Evan R.: The Diagnostic Yield of Histologic Examination of Seborrheic Keratoses. *Archives of Dermatology* 133: 1417–1420; 1997.

Eberlin, J. L.: Curetting for Seborrheic Keratoses (Letter). *Plastic and Reconstructive Surgery* 101(2): 546; 1998.

Epstein, E.: Treatment of Basal Cell Papillomas (Letter). *British Journal of Dermatology* 133: 492; 1995.

Fitzpatrick, Richard E.; Goldman, Michael P.; and Ruiz-Esparza, Javier: Clinical Advantage of the $CO_2$ Laser Superpulsed Mode. *Journal of Dermatologic Surgery and Oncology* 20: 449–456; 1994.

Giberson, Thomas P.; Kern, Joseph D.; Pettigrew, D. W. III; Eaves, Charles C.; and Haynes, John F. Jr.: Near-Fatal Hydrogen Peroxide Ingestion. *Annals of Emergency Medicine* 18(7): 778–779; 1989.

Gniadecka, Monika; Wulf, Hans C.; Nielsen, Ole F.; Christensen, Daniel H.; and Hercogova, Jana: Distinctive Molecular Abnormalities in Benign and Malignant Skin Lesions: Studies by Raman Spectroscopy. *Photochemistry and Photobiology* 66(4): 418–423; 1997.

Goette, Detlef K.: Basal Cell Carcinoma Arising in Seborrheic Keratoses. *Journal of Dermatologic Surgery and Oncology* 11: 1014–1016; 1985.

Goette, Detlef K.; Odom, Richard B.: Skin Blanching Induced by Hydrogen Peroxide. *Southern Medical Journal* 70(5): 620–622; 1977.

Googe, Paul B.; and King, Roy: Herpesvirus Infection of Seborrheic Keratoses. *The American Journal of Dermatopathology* 23(2): 146–148; 2001.

Gruber, Ronald P.; Vistnes, Lars; and Pardoe, Russel: The Effect of Commonly Used Antiseptics on Wound Healing. *Plastic and Reconstructive Surgery* 55(4): 476; 1975.

Marsh, Marylin; Comer, Gail M.; and Singer, Adam J.: Hydrogen Peroxide 3% Exposures. *Clinical Toxicology* 34(3): 323–327; 1996.

Humberston, C. Lynn; Dean, Bonnie S.; and Krenzelok, Edward P.: Ingestion of 35% Hydrogen Peroxide. *Clinical Toxicology* 28(1): 95–100; 1990.

Klein-Szanto, A. J. P.; and Slaga, T. J.: Effects of Peroxides on Rodent Skin: Epidermal Hyperplasia and Tumor Promotion. *The Journal of Investigative Dermatology* 79: 30–34; 1982.

Lemperle, Gottfried: Scratching Off Senile Warts (Letter). *Plastic and Reconstructive Surgery* 101(2): 546–547; 1998.

Long, C. C.; Motley, R. J.; and Holt, P. J. A.: Curettage of Small Basal Cell Papillomas with the Disposable Ring Curette is Superior to Conventional Treatment. *British Journal of Dermatology* 131: 732–733; 1994.

Long, C. C.; Motley, R. J.; and Holt, P. J. A.: Treatment of Basal Cell Papillomas (Letter Reply). *British Journal of Dermatology* 133: 492–493; 1995.

Miller, Willliam Thad: Multiple Giant Seborrheic Keratoses. *Plastic and Reconstructive Surgery* 101(2): 546; 1998.

Mohs, Frederic E.: Seborrheic Keratoses: Scarless Removal by Curettage and Oxidized Cellulose. *Journal of the American Medical Association* 212(11): 1956–1958; 1970.

Montgomery, Hamilton: Verruca Senilis and Keratoma Senile. *Minnesota Medicine* 18: 735–738; 1935.

Nanney, Lillian B.; Ellis, Darrell L.; Levine, Jeff; and King, Lloyd E.: Epidermal Growth Factor Receptors in Idiopathic and Virally Induced Skin Diseases. *American Journal of Pathology* 140(4): 915–925; 1992.

Nanney, Lillian B.; Gates, Ronald E.; Todderud, Gordon; King, Lloyd E. Jr.; and Carpenter, Graham: Altered Distribution of Phospholipase C-γ1 in Benign Hyperproliferative Epidermal Diseases. *Cell Growth and Differentiation* 3(4): 233–239; 1992.

Oliver, T. H.; and Murphy, D. V.: Influenzal Pneumonia: The Intravenous Injection of Hydrogen Peroxide. *The Lancet* ???: 432–433; 1920.

O'Toole, Edel A.; Goel, Mimi; and Woodley, David T.: Hydrogen Peroxide Inhibits Human Keratinocyte Migration. *Dermatologic Surgery* 22: 525–529; 1996.

Pumphrey, R. E.: Hydrogen Peroxide Proctitis. *American Journal of Surgery* 81: 60–68; 1951.

Rollman, O.; and Vahlquist, A.: Cutaneous Vitamin A Levels in Seborrheic Keratosis, Actinic Keratosis, and Basal Cell Carcinoma. *Archives of Dermatological Research* 270: 193–196; 1981.

Sanderson, K. V.: The Structure of Seborrheic Keratoses. *British Journal of Dermatology* 80: 588–593; 1968.

Scully, John P.: Treatment of Seborrheic Keratosis. *Journal of the American Medical Association* 213(9): 1498; 1970.

Snow, Stephen N.; Stiff, Mark A.; and Lambert, David R.: Scapel Sculpturing Techniques and Dermatologic Surgery. *Journal of Dermatologic Surgery and Oncology* 20(2): 120–126; 1994.

Sowden, J. M.; Lewis-Jones, M. S.; and Williams, R. B.: The Management of Seborrheic Keratoses by General Practitioners, Surgeons and Dermatologists. *British Journal of Dermatology* 139: 348–349; 1998.

Strohmer, Heinz; Öztürk, Dilek; and Egarter, Christian: Use of Hydrogen Peroxide for Vaginal Contraception. *Human Reproduction* 12(7): 1599–1604; 1997.

Sutton, Richard L.: The Symptomatology and Treatment of Seborrheic Keratoses. *Journal of the American Medical Association* 64(5): 403–408; 1915.

Tegner, Eva: Induction of Skin Blanching by Hydrogen Peroxide. *Acta Dermatologica Venereologica (Stockholm)* 74: 474–475; 1994.

Tegner, Eva; and Björnberg, Alf: Hydrogen Peroxide Cream for the Prevention of White Pressure Areas in UVA Sunbeds. *Acta Dermatologica Venereologica (Stockholm)* 70: 75–76; 1990.

Tur, Ethel; Bolton, Laura; and Constantine, Barry E.: Topical Hydrogen Peroxide Treatment of Ischemic Ulcers in the Guinea Pig: Blood Recruitment in Multiple Skin Sites. *Journal of the American Academy of Dermatology* 33: 217–221; 1995.

What is claimed is:

1. A method for treating seborrheic keratoses comprising:
   (a) obtaining a composition comprising hydrogen peroxide in a concentration of at least about 23 percent; and
   (b) applying said composition to a seborrheic keratosis on a seborrheic keratoses afflicted person or domesticated animal.

2. The method of claim 1, wherein the concentration of hydrogen peroxide is from about 35 percent to about 60 percent.

3. The method of claim 2, wherein the concentration of hydrogen peroxide is from about 60 percent to about 80 percent.

4. The method of claim 3, wherein the concentration of hydrogen peroxide is from about 40 percent to about 50 percent.

5. The method of claim 4, wherein the concentration of hydrogen peroxide is from about 43 percent to about 48 percent.

6. The method of claim 1, wherein the composition further comprises at least one vitamin.

7. The claim 6, wherein the vitamin may be selected from the group consisting of ascorbic acid, niacin, thiamin, and riboflavin.

8. The method of claim 7, wherein the vitamin is L-ascorbic acid.

9. The method of claim 1, wherein the composition further comprises at least one amino acid.

10. The method of claim 9, wherein the amino acid is selected from the group consisting of tyrosine, phenylalanine, carnitine, arginine, glycine, alanine, valine, leucine, isoleucine, serine, threonine, cysteine, cystine, methionine, asparagine, glutamine, lysine, 5-hydroxylysine, histidine, tryptophan, proline, omithine, and carnosine.

11. The method of claim 10, wherein the amino acid is L-carnitine.

12. The method of claim 1, wherein the composition further comprises at least one melanin inhibitor.

13. The method of claim 12, wherein the melanin inhibitor is selected from the group consisting of hydroquinone, niacinimide, cinnamic acid, gamma-L-glutamyl-L-cystine, gamma-L-cysteine, oxidized glutathione, phenol, polyphenol, linoleic acid, ellagic acid, glycyrrhizic acid, alkylsalicylic acid, kojic acid, kojic acid glycosides, kojic acid succinimide ester, kojic acid dimer, thiazoles, propionic acid, sulphur, kudzu root, lavanol, caffeic acid, dicaffeoylquinic acid, tricaffeoylquinic acid, vitamin K, hydantoin, tranexamic acid, chromone derivative, indomethicin methacin, erthorbic acid, glucoside, conchiolin hydrolyzate, licorice root extract, logwood extract, gromwell seed extract, arbutin, chitosan, superoxide dismutase, melanostatin, S-lactoyl glutathione, and hydroquinone glycoside.

14. The method of claim 13, wherein the melanin inhibitor is kojic acid.

15. The method of claim 1, wherein the composition further comprises at least one organic acid.

16. The method of claim 15, wherein the organic acid is selected from the group consisting of lactic acid, citric acid, isocitric acid, glycolic acid, malic acid, tartronic acid, tartaric acid, glucoronic acid, pyruvic acid, acetyl pyruvic acid, β-fluoropyruvic acid, 2-hydroxy isobutyric acid, galacturonic acid, salicylic acid, succinic acid, mandelic acid, β-phenyllactic acid, saccharic acid, β-phenylpyruvic acid, α-hydroxybutyric acid, α-hydroxyisobutyric acid, mucic acid, atrolactic acid, glucoheptonic acid, gluconic acid, glyceric acid, quinic acid, glyceruric acid, threuric acid, erythreuric acid, xyluric acid, lyxuric acid, arabinuric acid, riburic acid, iduric acid, guluric acid, mannuric acid, altruric acid, alluric acid, taluric acid, xylaric acid, lyxaric acid, trihydroxybutanoic acid, pentahydroxyhexanoic acid, and hexahydroxyheptanoic acid.

17. The method of claim 16, wherein the organic acid is L-lactic acid.

18. The method of claim 1, wherein the composition further comprises at least one hormone.

19. The method of claim 18, wherein the hormone is selected from the group consisting of dehydroepiandrosterone, progesterone, estrogen, melatonin, testosterone, pregnenolone, thyroid hormone, thymus hormone, and human growth hormone.

20. The method of claim 19, wherein the hormone is melatonin.

21. The method of claim 1, wherein the composition further comprises at least one sulfoxide.

22. The method of claim 21, wherein the sulfoxide is selected from the group consisting of dimethylsulfoxide and decylmethylsulfoxide.

23. The method of claim 22, wherein the sulfoxide is dimethylsulfoxide.

24. The method of claim 1, wherein the composition further comprises at least one alcohol.

25. The method of claim 24, wherein the alcohol is selected from the group consisting of ethanol, propanol, butanol, pentanol, hexanol, octanol, nonanol, decanol, 2-butanol, 2-pentanol, and benzyl alcohol.

26. The method of claim 25, wherein the alcohol is ethanol.

27. The method of claim 1, wherein the composition comprises at least one fatty acid.

28. The method of claim 27, wherein the fatty acid is selected from the group consisting of valeric acid, heptanoic acid, pelagonic acid, caproic acid, capric acid, lauric acid, myristic acid, stearic acid, oleic acid and caprylic acid.

29. The method of claim 28, wherein the fatty acid is myristic acid.

30. The method of claim 1, wherein the composition further comprises at least one fatty acid ester.

31. The method of claim 30, wherein the fatty acid ester is selected from the group consisting of isopropyl myristate, isopropyl palmitate, octyldodecyl myristate, ethyl acetate, butyl acetate, methyl acetate, methylvalerate, methylpropionate, diethyl sebacate, ethyl oleate.

32. The method of claim 31, wherein said fatty acid ester is isopropyl palmitate.

33. The method of claim 1, wherein the applying step is by brush, dropper, atomizer, injector, sprayer, occlusive patch or pipette.

34. The method of claim 1, wherein the composition further comprises at least one polyol.

35. The method of claim 34, wherein the polyol is selected from the group consisting of propylene glycol, polyethylene glycol, ethylene glycol, diethylene glycol, triethylene glycol, dipropylene glycol and glycerol.

36. The method of claim 34, wherein the polyol is propylene glycol.

37. The method of claim 1, wherein the composition further comprises at least one amide.

38. The method of claim 37, wherein the amide is selected from the group consisting of urea, dimethylacetamide, diethyltoluamide, dimethylformamide, dimethyloctamide, dimethyldecamide, hexamethylenelauramide, diethanolamine, and triethanolamine.

39. The method of claim 38, wherein the amide is dimethylformamide.

40. The method of claim 1, wherein the concentration of hydrogen peroxide is at least 40 percent.

41. The method of claim 1, wherein the composition further comprises at least one surfactant.

42. The method of claim 41, wherein the surfactant is selected from the group consisting of sodium laurate, sodium lauryl sulphate, cetyltrimethyl ammonium bromide, tetradecyltrimethylammonium bromide, benzalkonium chloride, octadecyltrimethylammonium chloride, cetylpyridinium chloride, dodecyltrimethylammonium chloride, hexadecyltrimethylammonium chloride, Poloxamer (231, 182, 184), Brij (30, 93, 96,99), Span (20, 40, 60, 80), Myrj (45, 51, 52), Miglyol 840, sodium cholate, sodium salts of taurocholic, glycolic, desoxycholic acids and lecithin.

43. The method of claim 42, wherein the surfactant is lecithin.

44. The method of claim 1, wherein the composition further comprises at least one terpene.

45. The method of claim 44, wherein the terpene is selected from the group consisting of D-limonene, α-pinene, β-carene, α-terpineol, terpinen-4-ol, carvol, carvone, pulegone, piperitone, menthone, cyclohexene oxide, limonene oxide, α-pinene oxide, cyclopentene oxide, 1,8-cineole, ylang ylang, anise, chenopodium and eucalyptus.

46. The method of claim 45, wherein the terpene is cyclohexene oxide.

47. The method of claim 1, wherein the composition further comprises at least one alkanone.

48. The method of claim 47, wherein the alkanone is selected from the group consisting of N-heptane, N-octane, N-nonane, N-decane, N-undecane, N-dodecane, N-tridecane, N-tetradecane, and N-hexadecane.

49. The method of claim 48, wherein the alkanone is N-octane.

50. The method of claim 1, wherein the composition further comprises at least one gamma linolenic precursor.

51. The method of claim 50, wherein the gamma linolenic acid precursor is selected from the group consisting of borage oil, black currant oil, and evening primrose oil.

52. A method for the removal of a seborrheic keratosis or seborrheic keratoses comprising:
(a) obtaining a composition comprising hydrogen peroxide in a concentration of at least 23 percent and at least one compound selected from a vitamin, an amino acid, a melanin inhibitor, an organic acid, a hormone, a sulfoxide, an alcohol, a fatty acid, a fatty acid ester, a polyol, an amide, a surfactant, a terpene, an alkanone, aloe vera, and a gamma linolenic precursor; and
(b) applying said composition to a seborrheic keratosis or seborrheic keratoses on a seborrheic keratosis or seborrheic keratoses afflicted person.

53. The method of claim 52, wherein the composition comprises about 26 percent hydrogen peroxide, about 2 percent kojic acid, about 12 percent dimethylsulfoxide, about 0.5 percent melatonin, about 1 percent L-ascorbic acid and about 15 percent ethanol.

54. The method of claim 52, wherein the composition comprises about 47 percent hydrogen peroxide, about 14 percent lactic acid, about 2 percent niacin, about 2 percent testosterone, about 1 percent licorice root extract, and about 0.5 percent β-phenylpyruvic acid.

55. The method of claim 52, wherein the composition comprises about 23 percent hydrogen peroxide, about 2 percent L-tyrosine, about 2 percent phenylalanine, about 1 percent tricaffeoylquinic acid, and about 18 percent ethanol.

56. The method of claim 52, wherein the composition comprises about 35 percent hydrogen peroxide and about 35 percent dimethylsulfoxide.

57. The method of claim 52, wherein the composition comprises about 35 percent hydrogen peroxide, about 0.5 percent L-ascorbic acid, about 0.5 percent niacin, about 0.5 percent glycine, about 0.5 percent hydroquinone, about 0.5 percent superoxide dismutase, about 5 percent galacturonic acid and about 14 percent ethanol.

58. The method of claim 52, wherein the composition comprises about 60 percent hydrogen peroxide and about 6 percent decylmethylsulfoxide.

59. The method of claim 52, wherein the composition comprises kojic acid, dimethylsulfoxide, melatonin, L-ascorbic acid and ethanol.

60. The method of claim 52, wherein the composition comprises hydrogen peroxide, lactic acid, niacin, testosterone, licorice root extract and β-phenylpyruvic acid.

61. The method of claim 52, wherein the composition comprises L-tyrosine, phenylalanine, tricaffeoylquinic acid and ethanol.

62. The method of claim 61, wherein the composition comprises about 23 percent hydrogen peroxide, about 2 percent phenylalanine, about 1 percent tricaffeoylquinic acid and about 18 percent ethanol.

63. The method of claim 52, wherein the composition comprises hydrogen peroxide, lactic acid, salicylic acid, citric acid, glycolic acid, and ethanol.

64. The method of claim 63, wherein the composition comprises about 23 percent hydrogen peroxide, about 4 percent lactic acid, about 4 percent glycolic acid, about 4 percent salicylic acid, about 4 percent citric acid and about 20 percent ethanol.

65. The method of claim 52, wherein the composition comprises dimethylsulfoxide.

66. The method of claim 52, wherein the composition comprises L-ascorbic acid, niacin, glycine, hydroquinone, superoxide dismutase, galacturonic acid and ethanol.

67. The method of claim 66, wherein the composition comprises about 35 percent hydrogen peroxide, about 0.5 percent L-ascorbic acid, about 0.5 percent glycine, about 0.5 percent hydroquinone, about 0.5 percent superoxide dismutase, about 5 percent galacturonic acid and about 14 percent alcohol.

68. The method of claim 52, wherein the composition comprises decylmethylsulfoxide.

69. The method of claim 68, wherein the composition comprises about 60 percent hydrogen peroxide and about 6 percent decylmethylsulfoxide.

70. The method of claim 1, wherein the composition further comprises aloe vera.

* * * * *